United States Patent [19]

Batorewicz et al.

[11] Patent Number: 4,518,803

[45] Date of Patent: May 21, 1985

[54] PROCESS FOR THE PREPARATION OF P-NITROSODIPHENYLAMINE

[75] Inventors: Wadim Batorewicz, New Haven; Edward L. Wheeler, Watertown, both of Conn.

[73] Assignee: Uniroyal, Inc., New York, N.Y.

[21] Appl. No.: 430,100

[22] Filed: Sep. 30, 1982

[51] Int. Cl.$^3$ .................. C07C 76/00; C07C 85/11
[52] U.S. Cl. ..................... 564/410; 564/420; 564/433
[58] Field of Search .............. 564/410, 420, 433

[56] References Cited

U.S. PATENT DOCUMENTS

| | | | |
|---|---|---|---|
| 3,340,302 | 9/1967 | Young | 564/433 X |
| 3,748,362 | 7/1973 | Kinstler | 564/410 |
| 4,034,042 | 7/1977 | Wedemeyer et al. | 564/410 |
| 4,313,002 | 1/1982 | Symon et al. | 564/410 X |
| 4,362,893 | 12/1982 | Kurek | 564/433 X |

Primary Examiner—Paul F. Shaver
Attorney, Agent, or Firm—Andrew D. Maslow

[57] ABSTRACT

A process is disclosed for the preparation of p-nitrosodiphenylamine hydrochloride comprising reacting diphenylamine, $C_5$–$C_{10}$ alkyl nitrite and anhydrous HCl in the presence of a $C_5$–$C_{10}$ aliphatic alcohol and essentially in the absence of an aromatic solvent.

12 Claims, No Drawings

PROCESS FOR THE PREPARATION OF P-NITROSODIPHENYLAMINE

FIELD OF THE INVENTION

This invention relates to an improved process for the preparation of p-nitrosodiphenylamine (pNDPA) from diphenylamine (DPA) and an alkyl nitrite in the presence of an excess of hydrogen chloride. The alkyl nitrite is derived from a primary aliphatic alcohol which is substantially immiscible with water, the said alcohol also serving as the reaction solvent. The resulting pNDPA hydrochloride slurry of the present process is unusually stable. After neutralization, the pNDPA is recovered by crystallization.

The pNDPA can be hydrogenated, without isolation from the solvent if desired, to p-aminodiphenylamine (pADPA), a known precursor for antioxidants and antiozonants, or reductively alkylated with an appropriate ketone to give the antiozonant directly.

BACKGROUND OF THE INVENTION

It is well known that pNDPA hydrochloride slurry is unstable. The instability of the pNDPA hydrochloride reaction slurry in the processes employing an alcohol and an aromatic solvent systems is well known to those skilled in the art, and is sometimes referred to as gelation. On occasion, due to localized overheating and possibly other factors, rapid decomposition has been observed in such two-solvent systems during the preparation of pNDPA hydrochloride. The pNDPA hydrochloride slurry decomposes even at room temperature. If kept over a period of time, a gradual darkening of the brick-red mixture is noted, and the viscosity of the reaction mass increases to the point that the recovery of the undecomposed product is no longer practical. For this reason, once the reaction is completed, the reaction mass is neutralized as quickly as possible.

The state of the prior art has been summarized in U.S. Pat. No. 4,034,042. The shortcomings of the previously disclosed processes as related to the instability of the pNDPA hydrochloride reaction mass are discussed therein in some detail. The improvement claimed in U.S. Pat. No. 4,034,042 is that the pNDPA hydrochloride is kept in solution by substantially increasing the ratio of the alcohol, usually methanol, to the aromatic hydrocarbon solvent. However, this solvent system does not stabilize pNDPA hydrochloride, but only moderates its decomposition so that the possibility of uncontrolled gelation is minimized. As a consequence, the reaction solution has to be neutralized as quickly as possible to prevent serious yield losses. As disclosed in U.S. Pat. No. 4,034,042, FIG. 1, the pNDPA hydrochloride in solution is about 50% decomposed in about four hours at 40° C.

It has been discovered that the pNDPA hydrochloride slurry made in accordance with our invention is very stable when higher saturated aliphatic alcohols, substantially immiscible with water, are employed as the process solvent. For example, pNDPA hydrochloride was prepared at temperatures as high as 50° C. without noticeable loss in yield. The type of rapid decomposition leading to gelation, does not occur when solvents of the present process are used.

DESCRIPTION OF THE INVENTION

The preparation of alkyl nitrites from alcohols is a known process to those skilled in the art. For example, the preparation of n-butyl nitrite from n-butanol is described in *Org. Synthesis,* Coll. Vol. 2, 1943, 108.

The alkyl nitrites of the present invention are usually prepared as 50% to 90% (by weight) solution in the alcohol. Normally, solutions of about 60% to 70% by weight are employed. For practical considerations, it is convenient, but not essential, to prepare the alkyl nitrite from the same alcohol as that to be used as a solvent for the process. This practice greatly simplifies the separation and recycling of the process solvent.

In the present process, a solution of an alkyl nitrite and a solution of DPA are combined. It is not essential, but convenient, to use the same alcohol as a solvent for the two reactants. To this stirred mixture is added, subsurface, an excess of hydrogen chloride, producing the pNDPA hydrochloride slurry of the present invention.

Conversely, the pNDPA hydrochloride of the present invention can be produced by incremental addition of an alkyl nitrite solution to a suspension of DPA hydrochloride in the alcohol also containing an appropriate excess of hydrogen chloride. By either procedure, a high yield of pNDPA hydrochloride is produced.

When preparing the DPA solution, the amount of the alcohol is adjusted, depending on the concentration of the nitrite solution employed, to give a pNDPA hydrochloride slurry having desired physical properties. The concentration of pNDPA hydrochloride obtained at the end of the reaction can vary from about 10% to about 40% by weight of the alcohol solvent. However, a 20% to 25% concentration is preferred. At this concentration, the reaction mass possesses good mixing and heat transfer properties. In addition, the resulting slurry is easy to handle in the subsequent work up operation.

It is not essential, but beneficial, to add hydrogen chloride and/or the alkyl nitrite at a fast rate commensurate with heat removal, and then allow the reaction to proceed to completion. The addition time may vary from about one to about five hours, preferably from two to three hours. The reaction mass is then stirred from one to five hours or longer if necessary, depending on the addition rate, the excess of hydrogen chloride employed and the temperature.

The presence of an excess of hydrogen chloride over DPA is necessary to drive the reaction to completion. The molar ratios of hydrogen chloride to DPA contemplated for the present process can vary from about 1.5:1 to about 2.5:1. The preferred ratio is from about 1.8:1 to 2.1:1.

It is also advantageous to employ a molar excess of the alkyl nitrite over DPA. The excess of the alkyl nitrite that can be employed varies from about 0.1 to 20 mole percent over DPA. The preferred molar excess is about 8 to 10 mole percent.

Nitrosation of DPA to give pNDPA hydrochloride is an exothermic process, so that some cooling is required, especially during the initial stage. The nitrosation can be carried out at temperatures ranging from about 20° C. to about 50° C. The preferred range is from about 30° C. to 35° C.

The saturated aliphatic alcohols useful as a solvent for the present invention can be primary or secondary, having from about $C_5$ to $C_{10}$ hydrocarbon chain which can be linear or branched, and having a b.p. in the range from about 130° C. to 200° C. Primary alcohols are preferred as a solvent for this process over the secondary alcohols because they are less prone to enter side reactions with h chloride, forming water and an alkyl chloride. A buildup of an alkyl chloride by-product in the recycled solvent may necessitate, eventually, removal of the by-product from the alcohol. In addition, even a small loss of the alcohol in this side reaction may adversely affect the economics on a commercial scale.

The preferred alcohols of the present invention are substantially immiscible with water. Small losses of the alcohol to the aqueous phase are economically unacceptable on a commercial scale and generally require burdensome separation procedures for the recovery of the solvent.

The preferred alcohols of the present process are primary saturated aliphatic alcohols having a $C_6$ to $C_8$ carbon atoms which can be linear or branched. Examples of such alcohols are n-hexanol, n-octanol and 2-ethylhexanol. The most preferred alcohol is hexanol.

When the reaction is completed, the pNDPA slurry is treated with an inorganic base, usually sodium hydroxide, to a pH from about 7 to about 14. Normally, it is preferred to stop the addition of the base when the pH of the mixture reaches a value of from about 8 to about 9. The mixture is heated to 70°-80° C. at which point essentially all of pNDPA is in solution in the alcohol. If necessary, the pH of the mixture is adjusted again to an 8 to 9 value with addition of more base. The aqueous phase is discarded, the alcohol phase is cooled and pNDPA recovered by crystallization.

EXAMPLE 1

Preparation of p-nitrosodiphenylamine hydrochloride

To a one-liter, 4-necked, round-bottomed flask equipped with a thermometer, a stirrer, an air condenser and a gas inlet tube was charged a solution of DPA (84.5 g, 0.5 mole) in hexanol (199 g). Then hexyl nitrite (68 g, 0.52 mole) was added as a 68% solution in hexanol. Addition of the hexyl nitrite generates a mild exotherm so that cooling in a water bath is required to keep the temperature below 40° C. Hydrogen chloride (38.3 g, 1.05 moles) is then introduced subsurface over a period of two hours while the reaction mass is agitated and kept at 30°-35° C., mostly at about 32° C., by means of an ice-water bath. The resultant brick-red slurry is stirred for an additional four hours while maintaining the temperature near 32° C. The pNDPA hydrochloride is separated by filtration, washed with hexane (200 ml) and air-dried at 60° C. Recovered 110.8 g. of pNDPA hydrochloride, m.p. 150° C., dec., 94.5% yield based on DPA.

EXAMPLE 2

Example 1 was repeated except that hexyl nitrite solution was added over a period of two hours to a mixture of DPA hydrochloride and hydrogen chloride in hexanol at 30°-35° C. The resulting brick-red slurry was stirred for four hours at about 32° C. The yield of pNDPA was essentially the same as in Example 1.

EXAMPLE 3

Preparation of p-nitrosodiphenylamine pNDPA hydrochloride was prepared according to the procedure of Example 1, but the salt was not isolated. Instead, the slurry was treated dropwise with a 14% solution of sodium hydroxide. The exotherm of neutralization was controlled by an ice-water bath so that the temperature of the reaction mass was not allowed to rise above 50° C. The addition of sodium hydroxide was stopped when the pH of the reaction mass reached a value of between 8 and 9. Stirring was continued for 30 minutes longer at 40°-50° C., then the mixture was heated to 70°-80° C. during which time the pH dropped below 7.

The pH was adjusted to about 8.5 by the addition of sodium hydroxide solution. While keeping the temperature at 70°-80° C., the aqueous phase was separated and discarded. The hexanol phase was kept overnight at about 5° C., and the bluish-black crystals of pNDPA were separated by filtration washed with hexane and air-dried at 60° C. overnight. Recovered 86.4 g of pNDPA, m.p. 143°-145° C. The mother liquors were concentrated to about 70 g by distillation under vacuum, and the solution kept at 5° C. overnight. Recovered 9.1 g of pNDPA, m.p. 139°-143° C. The combined yield is 96.5%, based on DPA.

EXAMPLE 4

The procedure of Example 3 was essentially followed using these ingredients:

| | |
|---|---|
| diphenylamine | 84.5 g (0.5 mole) |
| 2-ethylhexanol | 455 g |
| 2-ethylhexyl nitrite | 127 g (0.52 mole) as 68% solution in 2-ethylhexanol |
| HCl gas | 38.3 g (1.05 mole). |

After neutralization, the bluish-black crystals of p-nitrosodiphenylamine were isolated by filtration, washed with hexane and dried. 87 g of product was obtained (yield 87.9%, m.p. 142°-145° C.).

The alcohol phase of the mother liquor was separated from the aqueous phase and kept at room temperature for 48 hours, after which time bluish-black crystals were separated by filtration, washed with hexane and dried. An additional 6.0 g of product were thus obtained (m.p. 142°-145° C.). Total yield: 94.0%.

EXAMPLE 5

Again adopting the general procedure of Example 3, the following ingredients were used:

| | |
|---|---|
| diphenylamine | 84.5 g (0.5 mole) |
| n-pentanol | 207 g |
| n-pentyl nitrite | 60.8 g (0.52 mole) as 67% solution in pentanol |
| HCl gas | 38.3 g (1.05 mole). |

In this case, the neutralized p-nitrosodiphenylamine slurry was held at 5° C. for about 14 hours. The resultant crystals were isolated by filtration, washed with hexane and dried providing 88.6 g (89.5% yield) of product. Treating the mother liquor as previously described did not yield additional product.

EXAMPLE 6

Preparation of p-aminodiphenylamine pNDPA was prepared according to the procedure of Example 3, except that the product was not isolated; instead, the hexanol slurry was charged into a one-liter autoclave and hydrogenated over a 5% Pd/C catalyst (2.5 g) at a hydrogen pressure of from 500 to 800 psi at 60°-65° C. After about 30 minutes, the autoclave was cooled and the hexanol solution filtered to remove the catalyst and washed with water (2×300 ml). Hexanol and p-aminodiphenylamine were recovered by vacuum distillation. Collected 84 g of p-aminodiphenylamine which solidified to a light tan mass on cooling, m.p. 70°–72° C., 91% yield based on DPA.

We claim:

1. A process for the preparation of p-nitrosodiphenylamine hydrochloride comprising reacting diphenylamine, $C_5$–$C_{10}$ alkyl nitrite and anhydrous HCl in the presence of a $C_5$–$C_{10}$ aliphatic alcohol, essentially in the absence of an inert solvent and wherein the alkyl group of the alkyl nitrite has the same number of carbon atoms as said aliphatic alcohol.

2. The process of claim 1 further comprising converting p-nitrosodiphenylamine hydrochloride to p-nitrosodiphenylamine by the addition of a base.

3. The process of claim 2 further including the step of hydrogenating said p-nitrosodiphenylamine to p-aminodiphenylamine.

4. The process of claim 1 wherein said aliphatic alcohol is pentanol, hexanol or 2-ethylhexanol.

5. The process of claim 4 wherein said alkyl nitrite is pentyl nitrite, hexyl nitrite or 2-ethylhexyl nitrite.

6. The process of claim 1 wherein the molar ratio of HCl to diphenylamine is from 1.5/1 to 2.5/1.

7. A process for the preparation of p-nitrosodiphenylamine hydrochloride comprising reacting diphenylamine, $C_5$–$C_{10}$ alkyl nitrite and anhydrous HCl in the presence of a $C_5$–$C_{10}$ aliphatic alcohol, essentially in the absence of an inert solvent.

8. The process of claim 7 further comprising converting p-nitrosodiphenylamine hydrochloride to p-nitrosodiphenylamine by the addition of a base.

9. The process of claim 8 further including the step of hydrogenating said p-nitrosodiphenylamine to p-aminodiphenylamine.

10. The process of claim 7 wherein said aliphatic alcohol is pentanol, hexanol or 2-ethylhexanol.

11. The process of claim 10 wherein said alkyl nitrite is pentyl nitrite, hexyl nitrite or 2-ethylhexyl nitrite.

12. The process of claim 7 wherein the molar ratio of HCl to diphenylamine is from 1.5/1 to 2.5/1.

* * * * *